United States Patent [19]

Holden

[11] Patent Number: Plant 7,246

[45] Date of Patent: Jun. 12, 1990

[54] VARIETY OF GERANIUM NAMED BRIGETTE

[75] Inventor: Douglas Holden, Solvang, Calif.

[73] Assignee: Bodger Seeds, Ltd., El Monte, Calif.

[21] Appl. No.: 345,621

[22] Filed: Apr. 28, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

A new Geranium cultivar is distinguished by its leaf zoning, compact habit, mounding and spreading growth, the smallness and floriferousness of its orange-red flowers, its heat tolerance and its cutting production.

1 Drawing Sheet

BACKGROUND OF THE NEW PLANT

The present invention comprises a new and distinct cultivar of Pelargonium known by the varietal name Brigette (Oglevee No. 1310, Bodger No. 6GM 131-4). The new variety was discovered in a selective breeding program by Mr. Douglas Holden who set out to develop hybrid varieties for vegetative propagation. The new variety is a selection from the crossing of the seed parent, Salmon Floral Cascade, with the pollen parent, Rositta.

Salmon Floral Cascade is a commercially available vegetatively propagated cutting variety from Australia and which includes strains of *Pelargonium frutetorum* and *Pelargonium peltatum.* Rositta is a commercially available scarlet single flower zonal (*Pelargonium*×*hortorum*) $F_1$ hybrid seed geranium.

The new cultivar was discovered in August of 1986 at Bodger Seeds, Ltd., in El Monte, Calif., was first asexually reproduced by cuttings at Bodger Seeds, Ltd. at El Monte, Calif. and has been repeatedly asexually reproduced by cuttings at Oglevee Ltd. in Connellsville, Pa. It has been found to retain its distinctive characteristics through successive propagations.

The hybrid is a different color (orange-red) and has larger flowers than Salmon Floral Cascade.

The new cultivar, when grown in a glass greenhouse in Connellsville, Pa., using full light, 60° F. night temperature, 68° F. day temperature, 71° F. vent temperature, and grown in a soilless media of constant fertilizer of 200–250 parts per million nitrogen and potassium, has a response time from a rooted cutting to a flowering plant in a four inch (10 cm) pot of six weeks.

DESCRIPTION OF THE DRAWING

The accompanying drawing illustrates a new cultivar, the color being as nearly true as possible with color illustrations of this type.

DESCRIPTION OF THE NEW PLANT

The following detailed descriptions set foth to characteristics of the new cultivar. The data which define these characteristics were collected from asexual reproductions carried out by Oglevee Ltd. in Connellsville, Pa. The plant histories were taken on rooted cuttings, potted Aug. 1, 1988 and flowered Sept. 15, 1988 under full light in a greenhouse and color readings were taken indoors under 200–220 foot candles of cool white fluorescent light. Color references were primarily to the R.H.S. Colour Chart of The Royal Horticultural Society of London.

THE PLANT

Classification:

*Botanical.*—Hybrid species.

Form: Compact habit; semi-dwarf; lateral and procumbent growth.

Height: 17–18 cm from the media surface. p0 Growth: Self-branching, mound-like habit with some cascading growth.

Foliage: Zoning present, stalked leaf attachment.

Leaves:

*Size.*—5.5–6.5 cm across.

*Shape.*—Reniform, cordate base.

*Margin.*—Crenate.

*Texture.*—Pubescent; dull (not reflective).

*Color.*—Top: Green group 137A; Zone: Greyed-purple group 187A; Bottom: Green group 137C.

*Ribs and veins.*—Yellow-green group 147D; palmate venation.

Petioles: 5–8 cm in length; Yellow-Green group 146B.

Stem:

*Color.*—Yellow-green group 146C.

*Internodes.*—1–3 cm in length.

THE BUD

Shape: Upright; hemispherical cluster.

Size: 1.5–2 cm across.

INFLORESCENCE

Blooming habit: Continuous, upright, very floriferous blooming habit.

Size: 5–8 cm across.

Borne: 5–8 cm above foliage; florets on pedicel; pedicel on peduncle.

Florets:

*Form.*—Flat to slightly cupped.

*Color.*—Top — Red group 43B. Bottom — Red group 41B.

*Petals.*—10–15 in number; separate not united; margin entire obovate; smooth; flat to slightly cupped.

*Floret size.*—3.5–4.5 cm across.

*Texture and appearance.*—Smooth; slightly cupped.

Petaloids:

*Quantity.*—4–6.

*Shape.*—Narrow, elongated, twisted.

*Color.*—Red group 43A.

Pedicel: 2–3.5 cm in length. Yellow-green group 146C with a cast of Red-purple group 59B.

Peduncle: Arises from the node, opposite the leaf petiole; 16–20 cm in length.

*Color.*—Yellow-green group 146B with a cast of greyed-purple group 184A.

Disease resistance: None known.

Lasting quality: Stands up well in summer heat while continuing to bloom.

REPRODUCTIVE ORGANS

Stamens:

*Anthers.*—2 mm in length.

*Filaments.*—7–8 mm in length.

*Pollen.*—Golden brown.

Pistils:

*Number.*—1 with either 5 or 6 parted stigma.

*Length.*—6 mm.

*Stigma.*—5 or 6 parted, red-purple color.

*Style.*—3 mm; red-purple color.

Ovaries: Very pubescent, pale green; superior; 4 mm in length; 2 mm across.

Fruit: None noted.

This unique hybrid cross adds a new dimension to the Geranium family. The plant exhibits a neat mound habit that may be used in either hanging baskets or the traditional ground bed. The dark zone compliments the medium green foliage creating an eye catching novelty in the garden. Many small flower clusters create a large continuous bouquet of orange-red color. In comparing this new variety with the current Ivy varieties now on the market, one would find it more floriferous; a much fuller growth habit; better heat tolerance; and a much better cutting producer.

I claim:

1. A new and distinct variety of geranium plant substantially as shown herein, and characterized by its leaf zoning, compact habit, mounding and spreading growth, the smallness and floriferousness of its orange-red flowers, heat tolerance, and cutting production in comparison with current Ivy Geranium varieties.

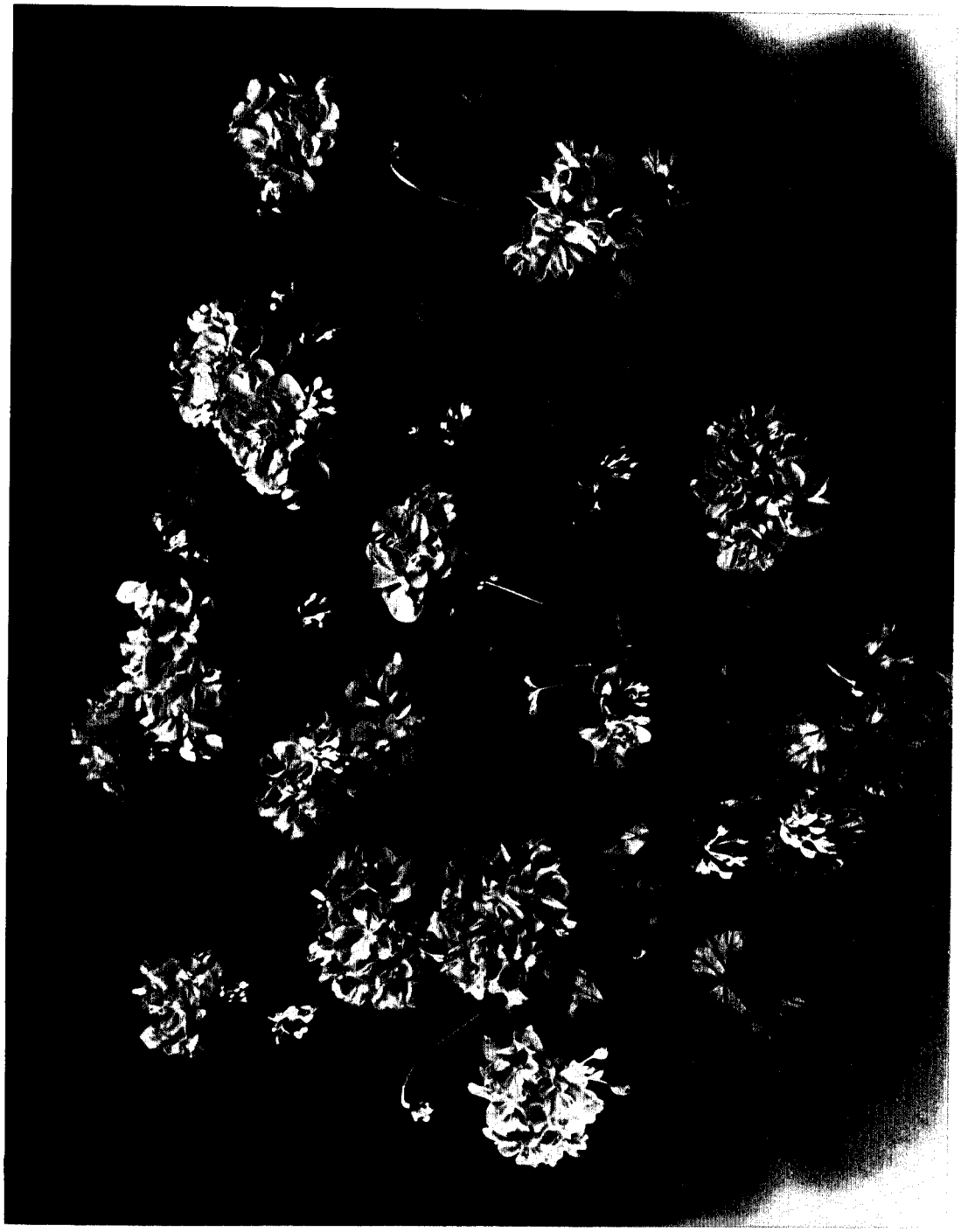

* * * * *